US011186660B2

(12) United States Patent
Wang et al.

(10) Patent No.: US 11,186,660 B2
(45) Date of Patent: *Nov. 30, 2021

(54) INTERNAL ELECTRON DONOR COMPOUND FOR PREPARING α-OLEFIN POLYMERIZATION CATALYST COMPONENT

(71) Applicants: YINGKOU XIANGYANG CATALYST CO., LTD, Liaoning (CN); DALIAN UNIVERSITY OF TECHNOLOGY, Liaoning (CN)

(72) Inventors: Licai Wang, Liaoning (CN); Zhanxian Gao, Liaoning (CN); Rubing Han, Liaoning (CN); Tianxiang Gao, Liaoning (CN); Qiuju Chen, Liaoning (CN); Limei Yu, Liaoning (CN); Wei Li, Liaoning (CN); Guotong Zheng, Liaoning (CN); Qingxin Dong, Liaoning (CN)

(73) Assignee: Yingkou Xiangyang Catalyst Co., Ltd.

( * ) Notice: Subject to any disclaimer, the term of this patent is extended or adjusted under 35 U.S.C. 154(b) by 336 days.

This patent is subject to a terminal disclaimer.

(21) Appl. No.: 16/368,718

(22) Filed: Mar. 28, 2019

(65) Prior Publication Data

US 2019/0218317 A1 Jul. 18, 2019

Related U.S. Application Data

(60) Division of application No. 15/132,050, filed on Apr. 18, 2016, which is a continuation-in-part of application No. PCT/CN2013/088843, filed on Dec. 9, 2013.

(30) Foreign Application Priority Data

Oct. 18, 2013 (CN) .......................... 201310495328.0

(51) Int. Cl.
*C08F 110/06* (2006.01)
*C07C 43/168* (2006.01)
*C07C 43/20* (2006.01)
*C07C 69/80* (2006.01)

(52) U.S. Cl.
CPC .......... *C08F 110/06* (2013.01); *C07C 43/168* (2013.01); *C07C 43/202* (2013.01); *C07C 69/80* (2013.01)

(58) Field of Classification Search
None
See application file for complete search history.

(56) References Cited

U.S. PATENT DOCUMENTS

| 10,287,371 B2 | 5/2019 | Wang et al. |
| 2012/0116031 A1 | 5/2012 | Chang |
| 2012/0277389 A1 | 11/2012 | Kim et al. |
| 2016/0229935 A1 | 8/2016 | Wang et al. |

FOREIGN PATENT DOCUMENTS

| CN | 1410457 A | 4/2003 |
| CN | 1831017 A | 9/2006 |
| CN | 1958621 A | 5/2007 |
| CN | 102040690 A | 5/2011 |
| CN | 102146146 A | 8/2011 |
| CN | 102234339 A | 11/2011 |
| CN | 103214602 A | 7/2013 |
| CN | 103554312 B | 8/2016 |
| WO | 2015054951 A1 | 4/2015 |

OTHER PUBLICATIONS

Wang, Licai; Advisory Action received for U.S. Appl. No. 15/132,050, filed Dec. 9, 2013 dated Dec. 14, 2017, 3 pgs.
Wang, Licai; Applicant Initiated Interview Summary received for U.S. Appl. No. 15/132,050, filed Dec. 9, 2013 dated Jun. 1, 2017, 2 pgs.
Wang, Licai; Final Office Action received for U.S. Appl. No. 15/132,050, filed Dec. 9, 2013 dated Sep. 5, 2017, 15 pgs.
Wang, Licai; Final Office Action received for U.S. Appl. No. 15/132,050, filed Dec. 9, 2013 dated Nov. 28, 2018, 9 pgs.
Wang, Licai; Issue Notification for U.S. Appl. No. 15/132,050, filed Apr. 18, 2016, dated Apr. 24, 2019, 1 pg.
Wang, Licai; Non-Final Office Action received for U.S. Appl. No. 15/132,050, filed Dec. 9, 2013 dated Feb. 1, 2017, 10 pgs.
Wang, Licai; Non-Final Office Action received for U.S. Appl. No. 15/132,050, filed Dec. 9, 2013 dated May 8, 2018, 7 pgs.
Wang, Licai; Notice of Allowance received for U.S. Appl. No. 15/132,050, filed Dec. 9, 2013 dated Feb. 25, 2019, 8 pgs.
Wang, Licai; Restriction Requirement received for U.S. Appl. No. 15/132,050, filed Dec. 9, 2013 dated Oct. 12, 2016, 9 pgs.
Wang, Licai; International Preliminary Report on Patentability received for serial No. PCT/CN2013/088843, filed Dec. 9, 2013, dated Apr. 28, 2016, 13 pgs (9 pages of English Translation and 4 pages of Official copy).

(Continued)

*Primary Examiner* — Yun Qian
(74) *Attorney, Agent, or Firm* — Taylor English Duma LLP

(57) ABSTRACT

An internal electron donor compound for preparing α-olefin polymerization catalyst component, including two kinds of electron donors; the proportion of the two kinds of electron donors in the compounding preparation of the catalyst is determined via designed experiments so as to obtain a catalyst component having good comprehensive performance or a particular performance. The electron donor compound of the present invention can be used in the preparation of α-olefin polymerization and co-polymerization catalyst component, particular the preparation of propylene polymerization catalyst component, and is applicable to prepare the propylene polymerization catalyst component by reacting magnesium chloride-ethanolscomlex compound carrier with titanium tetrachloride and electron donors, or to directly prepare the propylene polymerization catalyst component by reacting magnesium chloride, alcohols, titanium tetrachloride, and internal electron donor. In addition, also provided is a theoretical basis for selecting a proper electron donor combination from a plurality of electron donors.

12 Claims, 4 Drawing Sheets

(56) References Cited

OTHER PUBLICATIONS

Wang, Licai; International Search Report and Written Opinion received for serial No. PCT/CN2013/088843, filed Dec. 9, 2013, dated Jul. 23, 2014, 18 pgs (10 pages of English Translation and 8 pages of Official copy).
Wang, Licai; First Office Action for serial No. 201310495328.0, filed Feb. 5, 2014, dated Apr. 1, 2015, 21 pgs (13 pages of English Translation and 8 pages of Official copy).
Wang, Licai; First Search Report for serial No. 201310495328.0, filed Feb. 5, 2014, dated Mar. 25, 2015, 2 pgs (Official copy only).
Wang, Licai; Notification to Grant for serial No. 201310495328.0, filed Feb. 5, 2014 dated Jul. 4, 2016, 3 pgs (2 pages of English Translation and 1 page of Official copy).
Wang, Licai; Second Office Action for serial No. 201310495328.0, filed Feb. 5, 2014, dated Nov. 9, 2015, 25 pgs (15 pages of English Translation and 10 pages of Official copy).
Wang, Licai; Third Office Action for serial No. 201310495328.0, filed Feb. 5, 2014, dated Apr. 28, 2016, 12 pgs (7 pages of English Translation and 5 pages of Official copy).

INTERNAL ELECTRON DONOR COMPOUND FOR PREPARING α-OLEFIN POLYMERIZATION CATALYST COMPONENT

CROSS-REFERENCE TO RELATED APPLICATIONS

This is a division of U.S. application Ser. No. 15/132,050, filed Apr. 18, 2016, which is a continuation-in-part of PCT/CN2013/088843 filed Dec. 9, 2013, which claims priority to Chinese Application No. 201310495328.0, filed Oct. 18, 2013.

TECHNICAL FIELD

The present invention relates to an internal electron donor compound for preparing α-olefin polymerization catalyst component, belonging to the study field of α-olefin polymerization catalyst.

BACKGROUND OF THE INVENTION

Currently, Z-N catalyst is still the mainstream catalyst for olefins polymerization, Z-N catalyst for olefins polymerization, especially α-olefin polymerization, includes (1) titanium-containing magnesium chloride carrier catalyst component, (2) cocatalyst of organo-aluminum compound and (3) external electron donor for adjusting the poly-α-olefin's structure, wherein the titanium-containing magnesium chloride carrier catalyst component includes internal electron donor. In the present invention, the titanium-containing magnesium chloride carrier catalyst component shorts for catalyst component, there are two main methods for its preparation; one method is to firstly prepare magnesium chloride carrier, such as magnesium chloride-alcohols complex compound carrier, then carrying titanium and internal electron donor; the other method is directly reaction of magnesium chloride, alcohols, internal electron donor and titanium tetrachloride.

Internal electron donor plays a key role in regulating the activity of catalyst and poly-α-olefin's structure, and it is the core component of the catalyst component. However, the development of a practical internal electron donor is not easy, there are few internal electron donors that can be actually widely used which have limited performance, they cannot meet the growing demand for polyolefin industry. In recent years, it has been found that compound two or more kinds of electron donor as internal electron donor can get synergistic effect and obtain the performance different from single internal electron donor, which both have the advantages of two electron donors, and even produce new properties. The performance of the catalyst component, which compound two electron donors as internal electron donor, can be adjusted to get a catalyst component to meet the industrial demands. The preparation of catalyst component by compounding two electron donors as the internal electron donor is a new idea to develop a new catalyst component with excellent comprehensive performance or a certain excellent performance.

However, the preparation of catalyst component by compounding two electron donors as the internal electron donor is still in the experimental level by experiences, lack of rational methods to guide the research of internal electron donor compound catalyst component. It is not only unable to get the most desirable formula for preparing compound catalyst component and also causes the waste of internal electron donors. It is necessary to conduct a large amount of experiments to screen the good internal electron donor compounds, which may consume a lot of time, manpower and material resources.

To solve the above problems, the present invention establishes a method suitable to prepare catalyst component by compounding any two kinds of electron donors, and in particular discloses a method for preparing α-olefin polymerization catalyst component by compounding two electron donors as the internal electron donor, which is fast, accurate and practical.

SUMMARY OF THE INVENTION

The present invention selects five electron donors commonly used in industry (9,9-bis(methoxymethyl)fluorene, dibutyl phthalate, diisobutyl phthalate, 2,3-diisopropyl dibutyl succinate and 2,2'-dimethoxy-1,1'-binaphthyl) as examples, and provides a method for preparing catalyst component using electron donor compounds as the internal electron donor. The design and preparation method in the present invention are not limited to these five electron donors, it can be extended to any known electron donor used for the propylene polymerization catalyst component.

One of the technological purposes of the present invention is to provide an internal electron donor compound for preparing α-olefin polymerization catalyst component and the determine method of its ratio thereof; another technological purpose of the present invention is to provide a method for preparing propylene polymerization catalyst component using the internal electron donor compound to get catalyst components with a particular outstanding performance or good comprehensive performance.

The technological purposes of the present invention are achieved through the following technical solutions:

Compound of Internal Electron Donor

An internal electron donor compound for preparing α-olefin polymerization catalyst component, including two kinds of electron donors of A and B, wherein the ratio of A to B is determined according to the following method:

(1) Making load curves of A and B: preparing the catalyst component using A and B respectively as internal electron donor, determining the loading amount of each internal electron donor in the catalyst component's carrier and making two load curves of adding-loading amount respectively; the front sections of both the two load curves can be fitted to a straight line p; the middle sections of the two load curves are an arc line; and the rear sections of both the two load curves can be fitted to a straight line q, and the loading amounts of A and B at the intersections of straight lines p and q are a and b respectively and assuming a≥b; the loading amounts of A and B at the intersections of the straight line q and the arc line of the load curves are a+m and b+n respectively;

(2) Making compound competition load curves of A and B: preparing the catalyst component using the mixture of electron donors of A and B as internal electron donor; taking adding amount x of A and adding amount y of B to determine compound competition loading amount $x^i$ of A and compound competition loading amount $y^i$ of B in the catalyst component's carrier, and according to the values a and b obtained in step (1), selecting the points that meet the condition of $0<x^i<a$ and $0<y^i<b$ and $b≤x^i+y^i≤a$ to make compound competition load curve x-$x^i$ of A and compound competition load curve y-$y^i$ of B respectively;

(3) Respectively taking the loading amounts $x^k$ and $y^k$ of A and B the from two compound competition load curves $x$-$x^i$ and $y$-$y^i$ obtained in step (2), and design the loading amount by $b \leq x^k + y^k \leq a$, then taking the corresponding adding amounts of electron donors A and B on the compound competition load curves to prepare the catalyst component;

(4) Judging the compound result by using the catalyst component obtained in step (3) in alph-olefin polymerization, screening the catalyst component and determining the corresponding ratio of A to B;

(5) In addition, according to the result in step (4), determining the loading amounts of A and B in catalyst component are $x^j$ and $y^j$ respectively, adjusting $x^j$ and $y^j$ to $x^t$ and $y^t$ respectively, which should meet the condition of $x^j + y^j \leq x^t + y^t \leq x^j + y^j + m + n$, to make catalyst component and using it in α-olefin polymerization, judging the compound result, screening the catalyst component to determine another corresponding ratio of A to B.

The aforementioned straight lines p and q are the tangent line of the arc line of load curve's middle section, the intersection of tangent line p and arc line and the intersection of tangent line q and arc line are the point of tangency. The loading amounts of A and B corresponding to the points of tangency of straight line p and the arc line are the minimum amounts for the compound, and the loading amounts of A and B corresponding to the points of tangency of straight line q and the middle section arc line are a+m and b+n respectively, the points of tangency of tangent line q and the middle section arc line are the load saturation point, the values of a+m and b+n are the maximum amounts for the compound; and the intersections of straight lines p and q are the loading amounts a and b corresponding to A and B.

According to the internal electron donor compound m the present invention, for convenience narration, the point corresponding to loading amount a in the load curve of A in the step (1) is defined as a turning point, the same for load curve B. The catalyst component corresponding to the loading amount which is between line p's point of tangency and the turning point on the load curve doesn't have good performance. The catalyst component corresponding to the loading amount at the turning point on the curve has high catalytic activity and good comprehensive performance; the two catalyst components respectively corresponding to the points of a+m and b+n on the two load curves usually have good comprehensive performance, and their performances can provide direct information for preparing catalyst component by regulating compound of A and Bas internal electron donor. The adding amounts of A and B corresponding to a+m and b+n are the minimum amount necessary for preparing the catalyst component with good comprehensive performance.

FIG. 1 shows the load curve of 2,3-diisopropyl di butyl succinate.

It should be pointed out that, the compound competition load curve obtained in step (2) are not the same as the load curve of the same electron donor obtained in step (1), and the compound competition load curves are not same when the same electron donor compounds with different electron donors. FIG. 2 shows the load curve of 2,3-diisopropyl dibutyl succinate and its compound competition load curves with 9,9-bis(methoxymethyl)fluorene and dibutyl phthalate respectively, which present apparent differences.

According to the internal electron donor compound in the present invention, the α-olefin polymerization in step (4) is used to evaluate the performance of catalyst component, which is generally achieved through propylene polymerization. The catalyst component applicable for polymerization of propylene can be used in α-olefin polymerization such as 1-butene polymerization or co-polymerization of propylene and ethylene, etc., which is well-known to the skilled person in the art. The steps of propylene polymerization are as follows: in autoclave, using the mixture of external electron donor, cocatalyst and the catalyst component prepared by the present invention as catalyst to catalyze the propylene polymerization in a hydrogen condition; weighing the mass of polymer to calculate the activity of the catalyst and determining the polymer's performance of bulk density, isotacticity, melt index, and polymer molecular weight distribution, etc., so as to evaluate the performance of the catalyst component.

In step (3), take the loading amounts $x^k$ and $y^k$ corresponding to the two compound competition load curves obtained in step (2) as expected values of two kinds of electron donor compound loading amount, the actual loading amounts x' and y' in the catalyst for the two kinds of compound electron donors are basically consistent with the expected values, but the performances of catalyst components prepared by each group of compound internal electron donor have great difference. The expected catalyst component is selected by one or several kinds of performances as the standard, so as to get a catalyst component with a particular outstanding performance or good comprehensive performance, and respectively correspond to the ratio of different internal electron donor compounds. Usually the 15 expected catalyst component is selected by catalytic activity as the standard.

In actual operation, to avoid a large number of experiments, usually the values of $x^k$ and $y^k$ are selected within the greater range of the loading amount $b \leq x^k + y^k \leq a$, so as to select catalyst component with better performance, and its corresponding $x^j$ and $y^j$ are adjusted to $x^t$ and $y^t$ within a small range, usually within the range of $x^j + y^j \leq x^t + y^t \leq x^j + y^j + m + n$. The actual application value is: by adjusting the loading amounts of A and B within this range, a particular performance of the catalyst component will become outstanding, such as the bulk density of the polymer, or the comprehensive performance will become more superior.

According to the internal electron donor compound in the present invention, the common analytical methods are preferably used to determine the loading amount of internal electron donor in the catalyst component.

According to the internal electron donor compound in the present invention, the electron donor is preferably selected from the internal electron donor applicable for preparing propylene polymerization catalyst component.

According to the internal electron donor compound in the present invention, the two kinds of electron donors of A and B are preferably independently selected from the following internal electron donors, but A and B are different:

Aromatic monoesters electron donors: ethyl benzoate, ethyl p-methylbenzoate, ethyl p-Anisate, butyl benzoate, p-ethyl butyl benzoate, p-ethoxy butyl benzoate, etc.;

Aromatic diesters electron donors: dibutyl phthalate, dipropyl phthalate, dibutyl phthalate, diisobutyl phthalate, etc.;

Electron donors of dibenzoate-2,4-pentanediol esters: dibenzoate-2,4-pentanediol ester, di-m-chlorobenzoic-2,4-pentanediol ester, di-p-butylbenzoic-2,4-pentanediol ester, di-t-butylbenzoic-3-methyl-2,4-pentanediol ester, etc.;

Malanie esters electron donors: 2-(1-trifluoromethyl ethyl)-2-methyl diethyl malonate, 2-(1-trifluoromethyl ethylidene)diethyl malonate, 2-isopropylidene diethyl malonate, etc.;

Succinic acid esters electron donors: diethyl succinate, methyl diethyl succinate, 2,3-diisopropyl diethyl succinate, 2,3-diisopropyl-2-ethyl diethyl succinate, dibutyl succinate, 2,3-diisopropyldibutyl succinate, diisobutyl succinate, 2,3-diisopropyl diisobutyl succinate, etc.;

Glutarates electron donors: 3,3-diisobutyl diethyl glutarate, 3-isopropyl-3-methyl diethyl glutarate, 3,3-dimethyl diisobutylglutarate, 3-methyl diisobutylglutarate, 2-methyl-diethyl glutarate, diisobutylglutarate, etc;

Aromatic 1,3-diethers electron donors: 9,9-bis(methoxymethyl)fluorene, 5,5-bis(methoxymethyl)cyclopentadiene, etc.;

Aromatic 1,4-diethers electron donors: 2,2'-dimethoxy-1,1'-biphenyl, 2,2'-dimethoxy-1,1'-binaphthyl, 2,2'-dimethoxy-1,1'-biphenanthrol, etc;

Aliphatic 1,3-diethers electron donors: 2,2-diisopropyl-1,3-dimethoxypropane, 2,2-dibutyl-1,3-dimethoxypropane, 2,2-diisobutyl-1,3-dimethoxypropane, 2,2-di-t-butyl-1,3-dimethoxypropane, 2,2-diisoamyl-1,3-dimethoxypropane, 2,2-di-t-pentyl-1,3-dimethoxypropane, 2,2-diphenyl-1,3-dimethoxypropane, 2,2-dibenzyl-1,3-dimethoxypropane, 2-n-propyl-2-cyclohexyl-1,3-dimethoxypropane, 2-n-butyl-2-cyclohexyl-1,3-dimethoxypropane, 2-n-pentyl-2-cyclohexyl-1,3-dimethoxypropane, 2-isopentyl-2-isopropyl-1,3-dimethoxypropane, 2-isobutyl-2-isopropyl-1,3-dimethoxypropane, etc.;

Maleate esters electron donors: diethyl maleate, 2-cyclohexyl diethyl maleate, 2-isobutyl diethyl maleate, 2-n-amyl diethyl maleate, 2-cyclopentyl diethyl maleate, etc.;

According to the electron donor compounds in the present invention, the combination of two kinds of electron donors of A and B is preferably selected from one of the following combinations: 9,9-bis(methoxymethyl)fluorene and dibutyl phthalate, 9,9-bis(methoxymethyl)fluorene and diisobutyl phthalate, 9,9-bis(methoxymethyl)fluorene and 2,3-diisopropyl dibutyl succinate, 9,9-bis(methoxymethyl)fluorene and 2,2'-dimethoxy-1, 1'-binaphthyl, di butyl phthalate and 2,3-diisopropyl dibutyl succinate, dibutyl phthalate and 2,2'-dimethoxy-1,1'-binaphthyl, diisobutyl phthalate and 2,3-diisopropyl dibutyl succinate, diisobutyl phthalate and 2,2'-dimethoxy-1,1'-binaphthyl.

According to the electron donor compounds in the present invention, when selecting the electron donors, compound two electron donors with great distinction in their molecular structures, the competition loading amount is greatly different, the effect of adjusting the catalyst component performance is great also; means the greater the structural difference, the greater the adjusting effect; and the two electron donors with similar in their molecular structures, their competition loading amounts are similar, and the effect of adjusting the catalyst component performance is small. For example, compounding 9,9-bis(methoxymethyl)fluorene with 2,2'-dimethoxy-1,1'-binaphthyl as the internal electron donor, there are great distinction between the two load curves and competitive load curves, the three catalyst components obtained by the two individually or their compound as internal electron donor have great differences in catalytic performance, their compound as internal electron donor has apparent effect in adjusting the performance of the catalyst component, particularly the catalytic activity. Other above-mentioned combinations of compound as internal electron donor can also achieve the adjusting effect; to the contrary, the combination of dibutyl phthalate and diisobutyl phthalate has no obvious effect in adjusting the catalyst component's performance, and the catalyst component prepared by their compound has poor performance.

Preparation of Catalyst Component

Prepare α-olefin polymerization catalyst component with the electron donor compound according to the present invention, wherein the α-olefin polymerization catalyst component is α-olefin homopolymerization catalyst component and copolymerization catalyst component of α-olefin and ethylene.

According to the present invention, wherein the α-olefin polymerization catalyst component is propylene polymerization catalyst component.

According to the present invention, the propylene polymerization catalyst component is prepared by reacting magnesium chloride-ethanols complex compound carrier with titanium tetrachloride and the internal electron donor compound. The steps are as follows: using magnesium chloride-ethanols complex compound as a carrier, mix it with titanium tetrachloride at a ratio of 1 g:15-25 mL at the temperature of −20-−10° C., stirring and heating them to 110° C., and adding electron donor compound during the heating process of 30° C.-110° C., reacting 1-3 h at the temperature of 110° C., filtering and adding the same amount of titanium tetrachloride to react 1-3 h at the temperature of 110-120° C., washing and drying the product to obtain the propylene polymerization catalyst component.

In the above steps, the temperature from −20-−10° C. to 110° C. can be raised in segments to react. The two electron donors of compound can be added simultaneously or separately at any temperature within the range of 30° C.-110° C. During the preparation process of catalyst component, the titanium tetrachloride can be added by twice or three times, which both can meet the requirements.

According to the present invention, the propylene polymerization catalyst component can be directly prepared by reacting magnesium chloride, alcohols, the internal electron donor compound and titanium tetrachloride.

The catalyst component prepared by electron donor compound in the present invention is selected by propylene polymerization, which can be applied to polymerization of 1-butylene, also applied to co-polymerization of ethylene and propylene.

The beneficial effects of the present invention:

(1) The present invention from theory establishes a method for determining the ratio of two electron donors compound for preparing α-olefin polymerization catalyst component, and apply to prepare the load-type propylene polymerization catalyst component, and enhance scientificity and reduce blindness of experiments;

(2) The method provided in the present invention can be used to detect which combination has the better effect, the ordinary effect and the poorer effect when compound two kinds of electron donors to prepare the catalyst component;

(3) The method provided in the present invention determines the minimum adding amount of internal electron donor that can meet the maximum loading amount, so as to save the expensive internal electron donor significantly and avoid the wastes to minimize the costs for catalyst component synthesis;

(4) Using the method provided in the present invention to prepare the catalyst component of compound internal electron donor can save the experiment time, manpower and material resources;

(5) The method provided in the present invention has wide applications. It can be simultaneously applied to the two preparation methods of titanium-containing magnesium chloride carrier catalyst component, also can be applied to other preparation methods of olefin polymerization catalyst component.

DETAILED DESCRIPTION OF THE PREFERRED EMBODIMENTS

Figure 1:
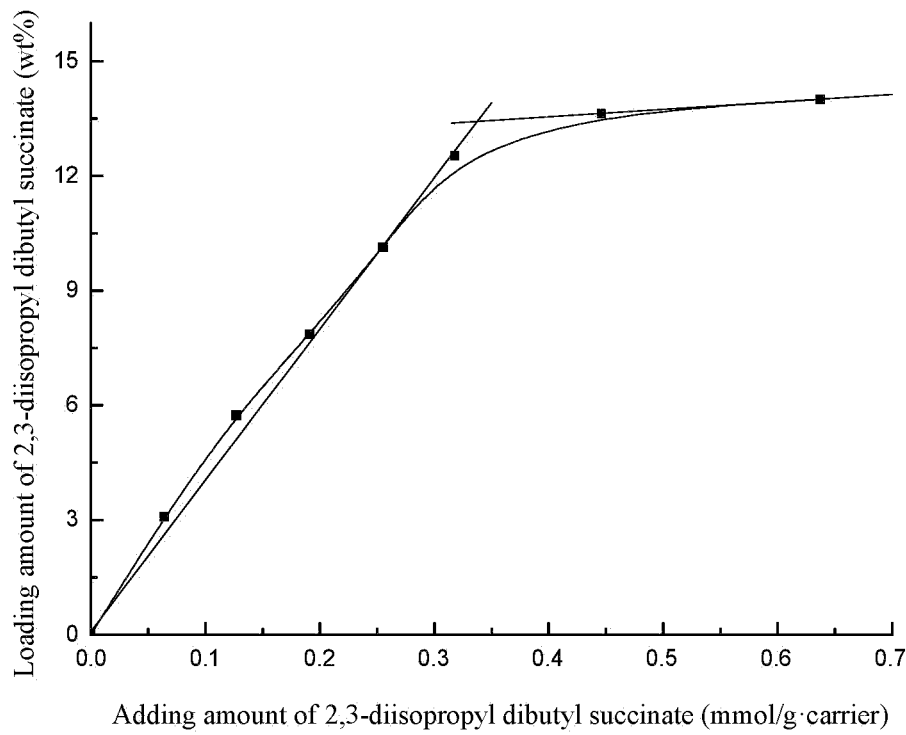
FIG. 1 shows the load curve of 2,3-diisopropyl di butyl succinate.
Figure 2:
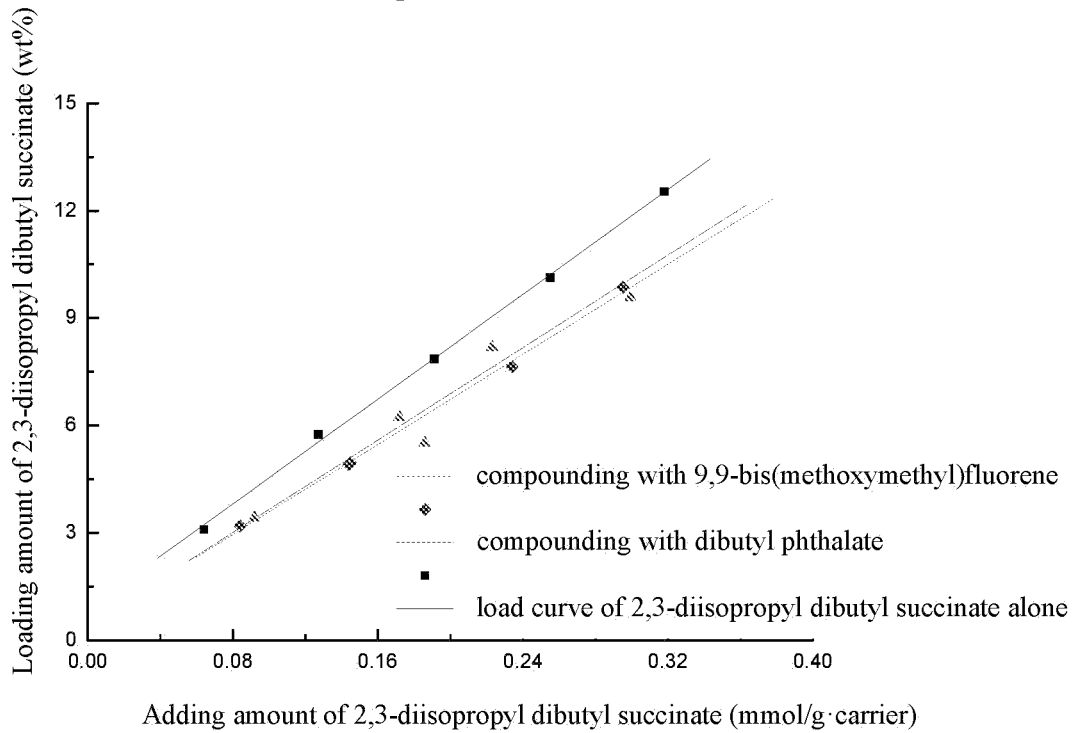
FIG. 2 shows the load curve of 2,3-diisopropyl dibutyl succinate and its compound competition load curves with 9,9-bis(methoxymethyl)fluorene and dibutyl phthalate respectively.

The following nonrestrictive embodiments can enable those ordinary persons skilled in the art to comprehensively understand the principle, process and method of the present invention, without limiting the present invention in any way.

Note: In the following embodiments, unless otherwise stated, the experiment operating procedures for preparation of catalyst component and determination of internal electron donor loading amount in the catalyst component and evaluation of catalyst component performance by propylene polymerization are carried out according to the following processes.

Preparation of Catalyst Component:

Add TiCl$_4$ into a dry glass reactor with nitrogen protection and cool it down to −20° C., add microsphere magnesium chloride-ethanols complex compound carrier (the ratio of magnesium to ethanols is 2.9:1) by stirring, the mixing ratio of carrier to TiCl$_4$ is 1 g:20 mL. Uniformly heat the aforementioned reaction mixture from −20° C. to 0° C., and then heat it to 70° C., add internal electron donor into the reactor (add two kinds of electron donors if compounding electron donors, and the detailed adding way please see the embodiments). Heat the reaction mixture to 110° C., and continue to react 2 h; suction filtrate the product, and add an equal amount of freshly-prepared TiCl4 again, heat them to 120° C. and continue to react 2 h, suction filtrate the product, wash the filter cake by hexane and dry it under vacuum condition to get a catalyst component.

Determination of loading amount of internal electron donor: determine the loading amount of internal electron donor in the catalyst component by using the commonly-used analytical method in industry.

Experiment operating procedures for evaluation of catalyst component performance by propylene polymerization:

Add successively 0.1 mL external electron donor of dicyclopentyldimethoxysilane and 4.0 mL cocatalyst of hexane solution of triethylaluminum (1 mol/L) and 0.005 mmol (calculated by titanium) catalyst component prepared by the present invention to a 2 L well-dried and propylene-replaced autoclave, import 1.5 L of liquid propylene and 0.2 MPa hydrogen, stir them at room temperature and mix uniformity, heat them to 70° C. and react 2 h with stirring, open the autoclave to take out the polypropylene, and cool it down to the room temperature; after the propylene is fully volatilized, weigh the mass of the product and calculate the activity of the catalyst, determine the polypropylene performance of isotacticity, bulk density, melt index, particle size distribution, and molecular weight distribution, etc.

Embodiment 1

Preparation of catalyst component with a single internal electron donor: using internal electron donor of 9,9-bis (methoxymethyl)fluorene as an example.

Prepare series of catalyst components by 9,9-bis (methoxymethyl)fluorene as internal electron donor, the adding amounts of 9,9-bis(methoxymethyl)fluorine are 0.08, 0.30, 0.45, 0.60, 0.75, 0.86, and 1.10 mmol/g·carrier respectively. Determine the loading amounts of 9,9-bis (methoxymethyl)fluorene in the catalyst components, which are 1%, 6%, 9%, 11.5%, 14.5%, 17.5%, and 17.6% respectively, and make the adding-loading amount load curves.

Carry out the operations same as the above preparation steps and prepare the catalyst components by dibutyl phthalate, diisobutyl phthalate, 2,3-diisopropyl dibutyl succinate, and 2,2'-dimethoxy-1, F-binaphthyl as the internal electron donors respectively. Determine the loading amounts of internal electron donors in the catalyst components, and make the adding-loading amount load curves respectively.

Figure 3:
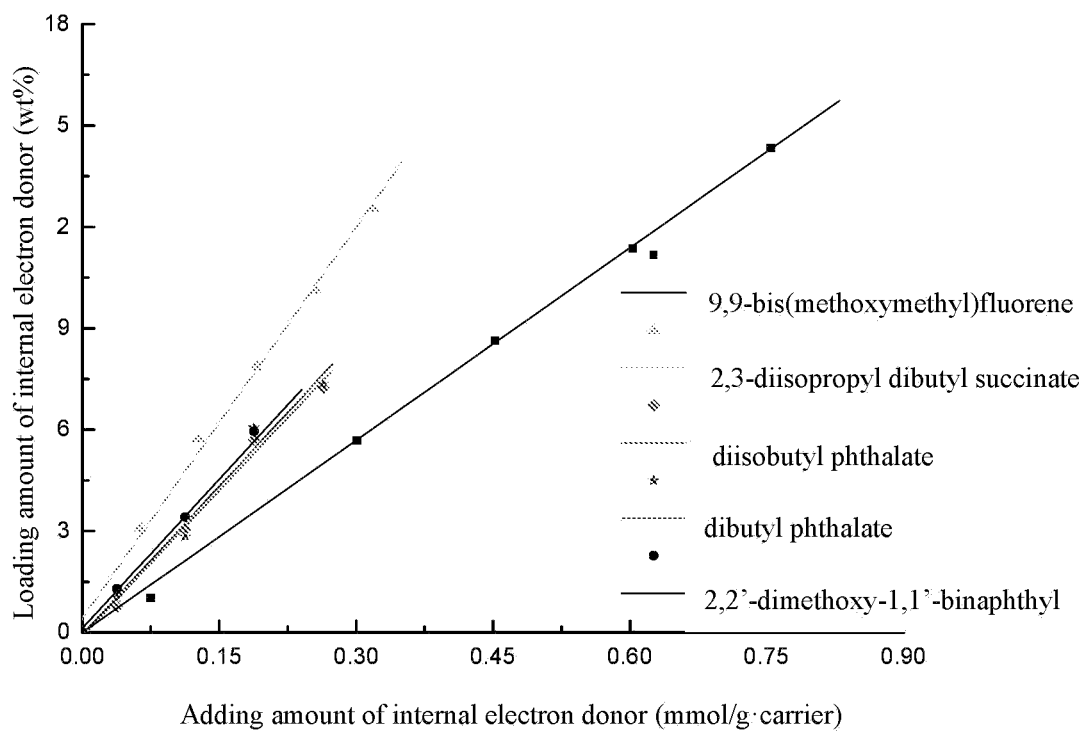
FIG. 3 shows the load curves of five electron donors in Embodiment I.

The load curves of these internal electron donors all can be fitted to two straight lines, which are connected by an arc line. FIG. 3 shows the straight lines of the five internal electron donors' load curves before the turning points, and the slopes of the straight lines are: 2,3-diisopropyl dibutyl succinate's slope>dibutyl phthalate's≈diisobutyl phthalate's>2,2'-dimethoxy-1,1'-binaphthyl's>9,9-bis (methoxymethyl)fluorene's. The loading amounts at the turning points are: 16% for 9,9-bis(methoxymethyl)fluorene, 14% for 2,3-diisopropyl dibutyl succinate, 8% for dibutyl phthalate, 8% for diisobutyl phthalate, and 7% for 2,2'-dimethoxy-1,1'-binaphthyl. In these cases, the catalyst components have high catalyst activity and better comprehensive performance.

Embodiment 2

Preparation of propylene polymerization catalyst component of two kinds of internal electron donors:

Compounding 9,9-bis(methoxymethyl)fluorene with dibutyl phthalate as an example.

When preparing catalyst component, the sum of the loading amounts of two kinds of electron donors are controlled within the range of 8%-16% according to FIG. 3. When heating the reaction mixture to 70° C., simultaneously add 9,9-bis(methoxymethyl)fluorene and dibutyl phthalate dissolved in toluene into the reaction mixture to prepare series of compound catalyst components, and determine their respective adding-loading amount competition load curve.

The above method is also applicable to the preparation of two kinds of internal electron donor catalyst components by the combinations of 9,9-bis(methoxymethyl)fluorene and diisobutyl phthalate, 9,9-bis(methoxymethyl)fluorene and 2,3-diisopropyl dibutyl succinate, 9,9-bis(methoxymethyl) fluorene and 2,2'-dimethoxy-1,1'-binaphthyl, di butyl phthalate and diisobutyl phthalate, dibutyl phthalate and 2,3-diisopropyl dibutyl succinate, dibutyl phthalate and 2,2'- dimethoxy-1,1'-binaphthyl, diisobutyl phthalate and 2,3-diisopropyl di butyl succinate, diisobutyl phthalate and 2,2'-dimethoxy-1,1'-binaphthyl; and control the compound loading amounts of 9,9-bis(methoxymethyl)fluorene and diisobutyl phthalate, 9,9-bis(methoxymethyl)fluorene and 2,3-diisopropyl dibutyl succinate, 9,9-bis(methoxymethyl)fluorene and 2,2'-dimethoxy-1,1'-binaphthyl, dibutyl phthalate and diisobutyl phthalate, dibutyl phthalate and 2,2'-dimethoxy-1,1'-binaphthyl, diisobutyl phthalate and 2,3-diisopropyl dibutyl succinate, diisobutyl phthalate and 2,2'-dimethoxy-1,1'-binaphthyl within 16%-8, 16%-14%, 16%-7%, 8%, 8%-7%, 14%-8%, 8%-7% respectively. Determine each internal electron donor's respective compound adding-loading amount competition load curve.

All the compound competition load curves are straight lines, but their slopes are not identical with that showed in FIG. 3, and the competitive load capacities of internal electron donors are as follow: 9,9-bis(methoxymethyl)fluorene>dibutyl phthalate≈diisobutylphthalate>2,3-diisopropyl di butyl succinate>2,2'-dimethoxy-1,1'-binaphthyl. The competitive load capacity of di butyl phthalate is equivalent to the diisobutyl phthalate's, and their respective compound loading value is identical to the loading value at the turning point, both about 8%.

Embodiment 3

Prepare catalyst component by the compound of 9,9-bis(methoxymethyl)fluorene (A) and 2,2'-dimethoxy-1,1'-binaphthyl (B) as internal electron donor.

Figure 4:
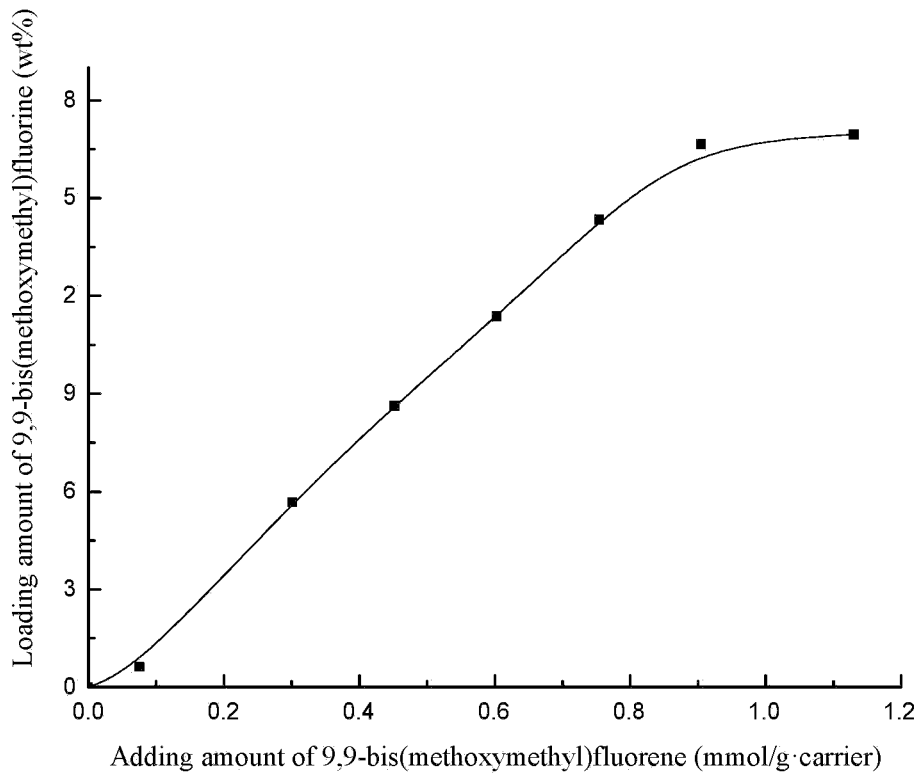
FIG. 4 shows the load curve of 9,9-bis(methoxymethyl) fluorene in Embodiment 3.
Figure 5:
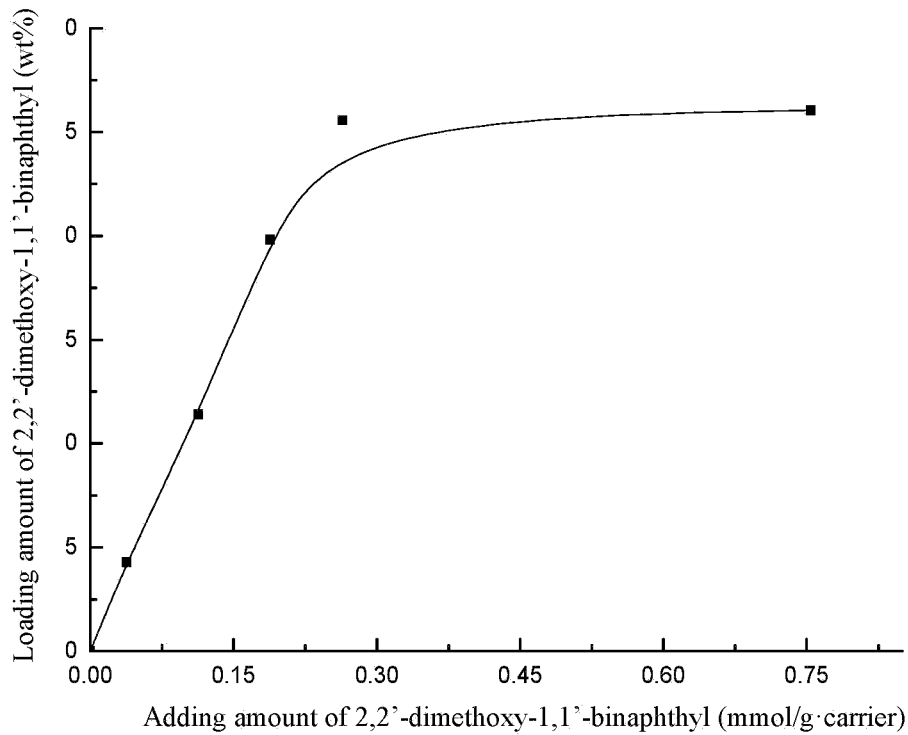
FIG. 5 shows the load curve of 2,2'-dimethoxy-1,1'-binaphthyl in Embodiment 3.
Figure 6:
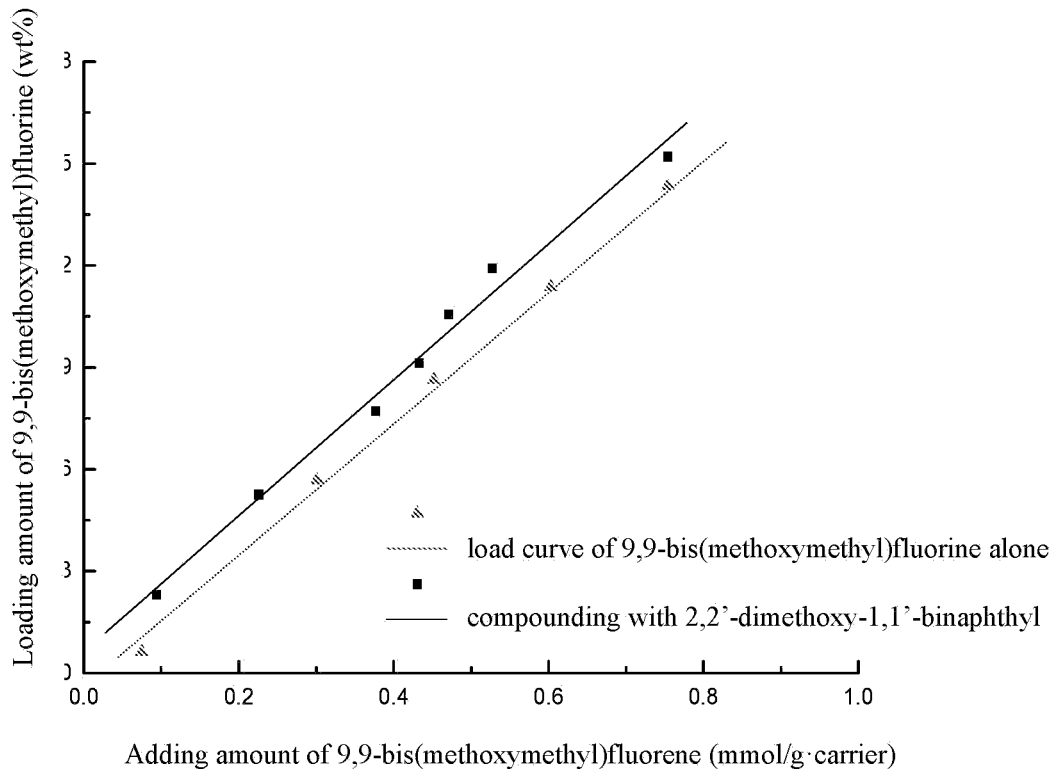
FIG. 6 shows the load curve of 9,9-bis(methoxymethyl) fluorene and its compound competition load curve with 2,2'-dimethoxy-1,1'-binaphthyl in Embodiment 3.
Figure 7:
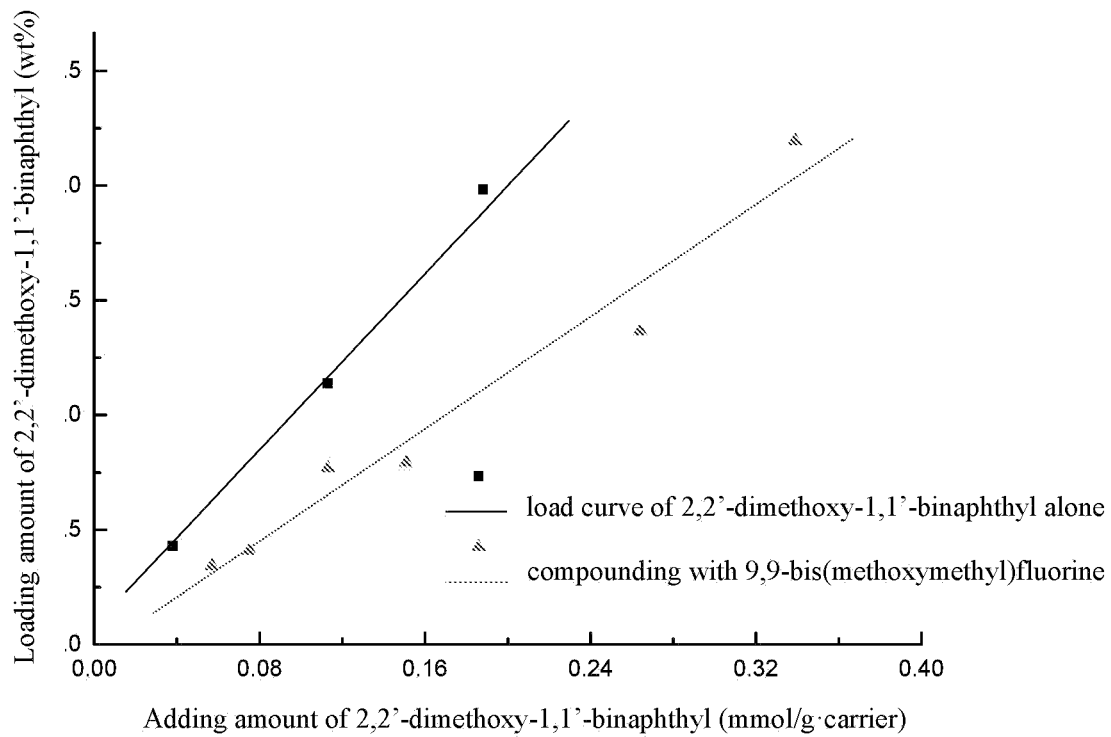
FIG. 7 shows the load curve of 2,2'-dimethoxy-1,1'-binaphthyl and its compound competition load curve with 9,9-bis(methoxymethyl)fluorene in Embodiment 3.

FIG. 4 shows the load curve of 9,9-bis(methoxymethyl)fluorene; FIG. 5 shows the load curve of 2,2'-dimethoxy-1,1'-binaphthyl; FIG. 6 shows the load curve of 9,9-bis(methoxymethyl)fluorene and its compound competition load curve with 2,2'-dimethoxy-1,1'-binaphthyl; FIG. 7 shows the load curve of 2,2'-dimethoxy-1,1'-binaphthyl and its compound competition load curve with 9,9-bis(methoxymethyl)fluorene;

Take values from the respective compound competition load curve of 9,9-bis(methoxymethyl)fluorene and 2,2'-dimethoxy-1,1'-binaphthyl obtained in embodiment 2 as the expected load values. According to the experiment results of embodiments 1 and 2, 9,9-bis(methoxymethyl)fluorene has a stronger competitive capacity, and its maximum loading amount is about 16%, thus control the total expected loading amount at 7%-16%. Prepare compound catalyst components, the part expected loading values and loading values of internal electron donor components and the performances of catalyst components are showed in table 1.

TABLE 1

Expected loading values and loading values of compounding A with B as internal electron donor, and the performances of catalyst components

| Total expected loading value of Di/% | Total adding amount of Di/ mmol · (g · carrier)$^{-1}$ | Loading amount of A/wt % | Loading amount of B/wt % | Catalyst activity/ kgPP · kgPP · (g · cat)$^{-3}$ | bulk density of PP/ gPP · cm$^{-3}$ | iso-tacticity of PP/% |
|---|---|---|---|---|---|---|
| 10.0 | 0.51 | 5.2 | 5.0 | 45 | 0.36 | 95.0 |
| 12.5 | 0.61 | 10.1 | 2.0 | 63 | 0.19 | 97.6 |
| 15.0 | 0.73 | 13.0 | 2.0 | 65 | 0.41 | 98.4 |
| 17.5 | 0.85 | 15.1 | 0.9 | 54 | 0.43 | 98.7 |

Note:
Di-internal electron donor; PP-polypropylene;
A—9,9-bis(methoxymethyl)fluorene;
B—2,2'-dimethoxy-1,1'-binaphthyl; hereinafter the same.

When the loading amount of 9,9-bis(methoxymethyl)fluorene is 13% and the loading amount of 2,2'-dimethoxy-1,1'-binaphthyl is 2% and the total loading amount is 15%, the activity of the catalyst is 65 kgPP·(g·cat)"1, which is applicable to the production, with good comprehensive performance, select the total loading amount of 15% as the expected catalyst component. When preparing this catalyst component, the adding amounts of the two kinds of electron donors are the ratio to be determined.

By adjusting the loading amounts of 9,9-bis(methoxymethyl)fluorene and 2,2'-dimethoxy-1,1'-binaphthyl within a small range of total loading amount of 15%, obtained the results in table 2.

TABLE 2

The component design of compounding A with B as internal electron donor, and the performances of catalyst components

| Expected loading amount of A/wt % | Expected loading amount of B/wt % | Loading amount of A/wt % | Loading amount of B/wt % | Catalyst activity/ kgPP · (g · cat)$^{-3}$ | bulk density of PP/ gPP · cm$^{-3}$ | iso-tacticity of PP/% |
|---|---|---|---|---|---|---|
| 8.0 | 7.0 | 7.9 | 5.9 | 60 | 0.39 | 97.2 |
| 10.0 | 5.0 | 10.2 | 4.3 | 64 | 0.40 | 97.4 |
| 11.0 | 4.0 | 10.9 | 3.6 | 64 | 0.40 | 97.9 |
| 12.0 | 3.0 | 11.2 | 2.7 | 66 | 0.41 | 98.1 |
| 14.0 | 1.0 | 14.2 | 0.9 | 67 | 0.41 | 98.2 |
| 14.0 | 2.0 | 13.5 | 1.8 | 65 | 0.41 | 98.8 |
| 15.0 | 1.0 | 15.5 | 0.8 | 68 | 0.42 | 98.6 |

As can be seen from table 2, when the loading amount of 9,9-bis(methoxymethyl)fluorene is 15.5% and the loading amount of 2,2'-dimethoxy-1,1'-binaphthyl is 0.8% and the total loading amount is 16.3%, the prepared catalyst component has the following performances: catalyst activity is 68 kgPP/g·cat; isotacticity of polypropylene is 98.6%, bulk density of polypropylene is 0.42 gPP/cm$^3$. In addition, the ethoxy content of this catalyst component measured is 0.8%, and this catalyst component is sensitive to hydrogen regulation, and the isotacticity of polypropylene is adjustable. Table 3 shows the carrier particle size distribution and catalyst component particle size distribution, and table 4 shows the polypropylene particle size distribution, and table 5 shows the polymer molecular weights and distributions. The morphology "duplication" phenomena of carrier, catalyst component and polypropylene are obvious.

TABLE 3

Particle size distribution of carrier and catalyst component

| Category | A/ wt % | B/ wt % | $D_{10}$/ μm | $D_{50}$/ μm | $D_{90}$/ μm | Particle size distribution index |
|---|---|---|---|---|---|---|
| Catalyst component | 15.5 | 0.8 | 23.2 | 42.2 | 73.1 | 1.18 |
| Carrier | — | — | 23.8 | 45.0 | 76.1 | 1.16 |

TABLE 4

Particle size distribution of polypropylene

| A/ wt % | B/ wt % | Polymer screening result/mm, % | | | | |
|---|---|---|---|---|---|---|
| | | >2.0 | 2.0-0.9 | 0.9-0.45 | 0.45-0.2 | <0.2 |
| 15.5 | 0.8 | 37.3 | 57.1 | 4.8 | 0.6 | 0.2 |

TABLE 5

Polymer molecular weight and distribution

| 1,3-ether/ wt % | 1,4-ether wt % | Number-average molecular weight | Weight-average Molecular Weight | z-average molecular weight | molecular weight distribution index |
|---|---|---|---|---|---|
| 15.5 | 0.8 | 47431 | 199427 | 494487 | 4.205 |

These performances are significantly different from the performances of catalyst components prepared by 9,9-bis (methoxymethyl) fluorene and 2,2'-dimethoxy-1,1'-binaphthyl as electron donor separately, for example, the catalytic activity of catalyst component prepared by 9,9-bis (methoxymethyl)fluorene as internal electron donor is 130 kgPP-/g·cat, and the catalytic activity of catalyst component prepared by 2,2'-dimethoxy-1,1'-binaphthyl as internal electron donor is 46 kgPP/g·cat.

Embodiment 4

Prepare catalyst component by the compound of 9,9-bis (methoxymethyl)fluorene and diisobutyl phthalate as internal electron donor:

According to the operating procedure of Embodiment 3, compound of 9,9-bis(methoxymethyl)fluorene and diisobutyl phthalate is designed as internal electron donor to prepare catalyst component. Through experiments, obtained the expected catalyst component with activity of 65 kgPP· (g·cat)$^{-1}$, and then slightly adjusting to get the optimal catalyst component, which loads 11.0% of 9,9-bis (methoxymethyl)fluorene and 3.9% of diisobutyl phthalate.

The steps for preparing the compound catalyst component are as follows: add 150 mL $TiCl_4$ into a dry glass reactor with nitrogen protection and cool it down to −20° C., add 10 g magnesium chloride-ethanols complex compound carrier by stirring, slowly raise the temperature to 70° C. Add 9,9-bis(methoxymethyl)fluorene (0.53 mmol/g·carrier), continue to raise the temperature to 110° C., and add diisobutyl phthalate (0.15 mmol/g·carrier) and react 2 h by stirring; suction filtrate the product, and add 150 mL $TiCl_4$ again, raise the temperature to 120° C. and react 1.5 h by stirring, suction filtrate the product, wash the filter cake five times by hexane at 60-65° C., and dry it under vacuum condition to get the catalyst component.

The optimal catalyst component loads 10.9% of 9,9-bis (methoxymethyl)fluorene and 3.3% of diisobutyl phthalate; its catalytic activity is 60 kgPP/g·cat, bulk density of polypropylene is 0.42 g/cm$^3$, the isotacticity is 97.5%, and the melting index is 2.85 g/10 min.

Embodiment 5

Figure 8:
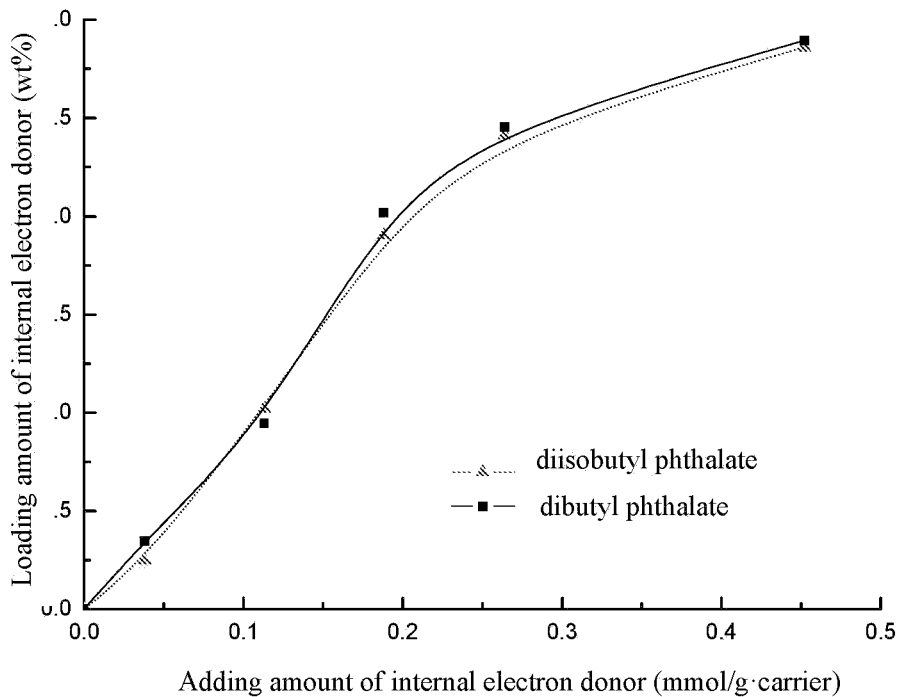
FIG. 8 shows the load curves of two kinds of electron donors in Embodiment 5.

Prepare catalyst component by the compound of dibutyl phthalate (A) and diisobutyl phthalate (B) as internal electron donor:

According to the operating procedure of Embodiment 3, compound of dibutyl phthalate and diisobutyl phthalate is designed as the internal electron donor to prepare the catalyst component, table 6 shows the results. FIG. 8 shows the load curves of di butyl phthalate and diisobutyl phthalate, and the two curves have no great difference.

As shown in table 6, no matter for the loading amounts of A and B or the compound competition loading amounts of A and B, or the performances of catalyst components when A or B alone or A and B compounding as internal electron donor, it does not show the apparent advantages of dibutyl phthalate and diisobutyl phthalate compounding as internal electron donor to prepare catalyst component.

TABLE 6

Results of dibutyl phthalate and diisobutyl phthalate compounding as internal electron donor to prepare catalyst component

| Adding amount/mmol (g·carrier)$^{-1}$ | | | Loading amount/ wt % | | | catalyst activity kgPP· (g·cat)$^{-1}$ | isotacticity of PP/% | bulk density of gPP/ cm$^{-3}$ | Melt index/ gPP· min$^{-1}$ |
|---|---|---|---|---|---|---|---|---|---|
| A | B | A + B | A | B | A + B | | | | |
| — | 0.36 | 0.36 | — | 5.68 | 5.68 | 46.2 | 95.57 | 0.43 | 5.5 |
| 0.36 | — | 0.36 | 6.60 | — | 6.60 | 48.5 | 95.78 | 0.44 | 5.6 |
| 0.12 | 0.24 | 0.36 | 2.10 | 4.35 | 6.45 | 47.4 | 95.21 | 0.43 | 2.7 |
| 0.18 | 0.18 | 0.36 | 3.44 | 2.54 | 5.98 | 48.3 | 94.78 | 0.43 | 2.7 |

Embodiment 6

Prepare catalyst component by directly reacting magnesium chloride, alcohols, internal electron donor and titanium tetrachloride:

Taking 9,9-bis(methoxymethyl)fluorene and diisobutyl phthalate as internal electron donor compound as an example, the steps for preparing catalyst component are as follows:

a) Preparation of Ethanols Complex Compound

Add 5 g anhydrous $MgCl_2$ and 30 mL decane and 23 mL 2-ethyl hexanol into the three-necked flask equipped with stirrer and thermometer which is sufficiently replaced with nitrogen gas, raise the temperature to 130° C. by stirring, and continue to react 2 h. Add 1.5 mL tetrabutyltitanate and 2 mL diisobutyl phthalate to 5 mL toluene beforehand, and react 0.5 h at room temperature to get complex compound solution. Add this toluene solution into the three-necked flask and continue to react 1 h at 130° C., cool it down to room temperature to form a stable ethanols complex compound solution.

b) Preparation of the Catalyst Component

Dropwise add the above prepared ethanols complex compound solution within 30 min into a reactor (containing 200 mL titanium tetrachloride and maintained at a temperature of −20° C.) equipped with stirrer and thermometer and sufficiently replaced with nitrogen gas. After dropwise add is completed, raise the temperature to 70° C., and add 0.5 g 9,9-bis(methoxymethyl)fluorene which dissolved in 10 mL toluene, continue to raise the temperature to 110° C., and add 1.0 mL diisobutyl phthalate and continue to react 2 h. After the liquid is filtered, add 200 mL titanium tetrachloride again and react 1.5 h at 110° C. Filter to obtain the resultant and wash it with trichloromethane for 60 min at 60° C., and then wash it with hexane until there is no free chloride ion in the filtrate, get the catalyst component after vacuum drying.

The catalyst component was measured that it contains 9.5% of 9,9-bis(methoxymethyl)fluorene and 4.6% of diisobutyl phthalate.

The catalyst activity measured by propylene polymerization is 56 kg PP/g·cat, the bulk density of polymers is 0.42 g/cm³%, and the polymer isotacticity is 98.5%.

We claim:

1. A method of preparing an α-olefin polymerization catalyst having a component comprising electron donor A and electron donor B, wherein electron donor A and electron donor B have a ratio determined by a method comprising:

(1) adding an amount ("adding amount") of the internal electron donor A to a catalyst carrier and measuring a corresponding amount loaded to the catalyst carrier ("load amount") of the internal electron donor A;

(2) repeating step (1) to obtain a plurality of the adding amounts and the corresponding load amounts of the internal electron donor A, and constructing a first load curve showing a relationship between the adding amounts (x-axis) and the corresponding load amounts (y-axis) of the internal electron donor A, x-axis and y-axis forming a coordinate plane;

(3) adding an amount ("adding amount") of the internal electron donor B into the catalyst carrier and measuring a corresponding amount loaded to the catalyst carrier ("load amount") of the internal electron donor B;

wherein A and B are mixed internal electron donors, the adding amount of A is x, the adding amount of B is y, A has a competition load amount $x^i$, and B has a competition load amount $y^i$;

(4) repeating step (3) to obtain a plurality of the adding amounts and the corresponding load amounts of the internal electron donor B, and constructing a second load curve showing a relationship between the adding amounts (x-axis) and the corresponding load amounts (y-axis) of the internal electron donor B, x-axis and y-axis forming a coordinate plane and constructing a competition curve of the adding amount of A (x) versus the load amount of A ($x^i$), $x-x^i$;

(5) fitting the first load curve by a least squares method by drawing a straight line p1 in a front portion passing a point where the adding amount and the load amount both read zero ("zero point"), drawing a straight line q1 in a rear portion passing the end point of the first load curve, and drawing a first arc line between the front portion and the rear portion of the first load curve and constructing a competition curve of the adding amount of B (y) versus the load amount of B ($y^i$), $y-y^i$;

(6) fitting the second load curve by a least squares method by drawing a straight line p2 in a front portion passing a point where the adding amount and the load amount both read zero ("zero point"), drawing a straight line q2 in a rear portion passing the end point of the load curve, and drawing a second arc line in between the front portion and the rear portion of the second load curve, wherein an intersection of p1 and q1 has a load amount of a, wherein an intersection of p2 and q2 has a load amount of b, and a≥b, wherein an intersection of q1 and the first arc line has a load amount of a+m and an intersection of q2 and the second arc line has a load amount of b+n;

(7) mixing an adding amount x of A and an adding amount y of B with the catalyst carrier;

(8) measuring a compound competition load amount of A loaded to the catalyst carrier as $x^i$ and a compound competition load amount of B loaded to the catalyst carrier as $y^i$, wherein $0<x^i<a$ and $0<y^i<b$ and $b\le x^i+y^i\le a$, (9) constructing a first compound competition load curve for the internal electron donor A and a second compound competition load curve for the internal electron donor B;

(10) respectively selecting a load amount $x^k$ of the internal electron donor A from the first compound competition load curve and a load amount $y^k$ of the internal electron donor B from the second compound competition load curve, wherein $b\le x^k+y^k\le a$;

(11) determining the adding amount of the internal electron donor A corresponding to $x^k$ based on the first compound competition load curve and the adding amount of the internal electron donor B corresponding to $y^k$ based on the second compound competition load curve;

(12) preparing the catalyst component by adding to the carrier the adding amount of the internal electron donor A corresponding to $x^k$ and the adding amount of the internal electron donor B corresponding to $y^k$;

(13) testing the catalyst component obtained in step (12) in α-olefin polymerization, screening the catalyst component and determining the corresponding ratio of A to B; and

(14) determining the load amounts of A and B in catalyst component as being $x^i$ and $y^i$, respectively; adjusting $x^i$ and $y^i$ to $x^t$ and $y^t$, respectively, provided that amount sum $x^i+y^i$ follows a formula $x^i+y^i \le x^t+y^t \le a+m+b+n$ to prepare the catalyst component and testing the catalyst component in α-olefin polymerization, and determining the corresponding ratio of A and B, wherein lines p1 and p2 pass the zero point of the coordinate plane, line q1 passes the end point of the first load curve, line q2 passes the end point of the second load curve, wherein the adding amount is the amount of the internal electron donor A or B added to the carrier, the load amount is the amount of the internal electron donor A or B loaded onto the carrier when only A or B is added to the carrier, and the competition load amount is the amount of the internal electron donor A or B loaded onto the carrier when both A and B are added to the carrier;

wherein the internal electron donors A and B are different and independently selected from the group consisting of ethyl benzoate, ethyl p-methylbenzoate, ethyl p-Anisate, butyl benzoate, p-ethyl butyl benzoate, p-ethoxy butyl benzoate, dibutyl phthalate, diisobutyl phthalate, dibenzoate-2,4-pentanediol ester, di-m-chlorobenzoic-2,4-pentanediol ester, di-p-butylbenzoic-2,4-pentanediol ester, di-t-butylbenzoic-3-methyl-2,4-pentanediol ester, 2-(1-trifluoromethyl ethyl)-2-methyl diethyl malonate, 2-(1-trifluoromethyl ethylidene)diethyl malonate, 2-isopropylidene diethyl malonate, diethyl succinate, methyl diethyl succinate, 2,3-diisopropyl-2-ethyl diethyl succinate, dibutyl succinate, 2,3-diisopropyl dibutyl succinate, diisobutyl succinate, 2,3-diisopropyl diisobutyl succinate, 3,3-diisobutyl diethyl glutarate, 3-isopropyl-3-methyl diethyl glutarate, 3,3-dimethyl diisobutylglutarate, 3-methyl diisobutylglutarate, 2-methyl-diethyl glutarate, diisobutylglutarate, 9,9-bi s(methoxymethyl)fluorene, 5,5-bis(methoxymethyl)cyclopentadiene, 2,2'-dimethoxy-1,1'-biphenyl, 2,2'-dimethoxy-1,1'-binaphthyl, 2,2'-dimethoxy-1,1'-biphenanthrol, 2,2-diisopropyl-1,3-dimethoxypropane, 2,2-dibutyl-1,3-dimethoxypropane, 2,2-diisobutyl-1,3-dimethoxypropane, 2,2-di-t-butyl-1,3-dimethoxypropane, 2,2-diisoamyl-1,3-dimethoxypropane, 2,2-di-t-pentyl-1,3-dimethoxypropane, 2,2-diphenyl-1,3-dimethoxypropane, 2,2-dibenzyl-1,3-dimethoxypropane, 2-n-propyl-2-cyclohexyl-1,3-dimethoxypropane, 2-n-butyl-2-cyclohexyl-1,3-dimethoxypropane, 2-n-pentyl-2-cyclohexyl-1,3-dimethoxypropane, 2-isopentyl-2-isopropyl-1,3-dimethoxypropane, 2-isobutyl-2-isopropyl-1,3-dimethoxypropane, diethyl maleate, 2-cyclohexyl diethyl maleate, 2-isobutyl diethyl maleate, 2-n-amyl diethyl maleate, and 2-cyclopentyl diethyl maleate, and wherein the carrier comprises $MgCl_2$.

2. The method according to claim 1, wherein the electron donors A and B are applicable for preparing propylene polymerization catalyst component.

3. The method according to claim 2, wherein the internal electron donors A and B are different and independently selected from the group consisting of 9,9-bis(methoxymethyl)fluorene, dibutyl phthalate, diisobutyl phthalate, 2,3-diisopropyldibutyl succinate, and 2,2'-dimethoxy-1,1'-binaphthyl.

4. The method according to claim 2, wherein a combination of internal electron donors A and B is one of the following combinations: 9,9-bis(methoxymethyl)fluorene and dibutyl phthalate, 9,9-bis(methoxymethyl)fluorene and diisobutyl phthalate, 9,9-bis(methoxymethyl)fluorene and 2,3-diisopropyldibutyl succinate, 9,9-bis(methoxymethyl)fluorene and 2,2'-dimethoxy-1,1'-binaphthyl, dibutyl phthalate and 2,3-diisopropyldibutyl succinate, dibutyl phthalate and 2,2'-dimethoxy-1,1'-binaphthyl, diisobutyl phthalate and 2,3-diisopropyldibutyl succinate, or diisobutyl phthalate and 2,2'-dimethoxy-1,1'-binaphthyl.

5. The method according to claim 1, wherein a combination of the internal electron donors A and B is one of the following combinations: 9,9-bis(methoxymethyl)fluorene and dibutyl phthalate, 9,9-bis(methoxymethyl)fluorene and diisobutyl phthalate, 9,9-bis(methoxymethyl)fluorene and 2,3-diisopropyldibutyl succinate, 9,9-bis(methoxymethyl)fluorene and 2,2'-dimethoxy-1,1'-binaphthyl, dibutyl phthalate and 2,3-diisopropyldibutyl succinate, dibutyl phthalate and 2,2'-dimethoxy-1,1'-binaphthyl, diisobutyl phthalate and 2,3-diisopropyldibutyl succinate, or diisobutyl phthalate and 2,2'-dimethoxy-1,1'-binaphthyl.

6. The method according to claim 1, wherein the internal electron donor A or B is 2,2'-dimethoxy-1,1'-binaphthyl or 2,3-diisopropyl dibutyl succinate.

7. The method according to claim 1, wherein the internal electron donor A or B is 2,2'-dimethoxy-1,1'-binaphthyl or 9,9-bis(methoxymethyl)fluorene.

8. The method according to claim 1, wherein the α-olefin polymerization catalyst component is homopolymerization catalyst component of α-olefin and co-polymerization catalyst component of α-olefin and ethylene.

9. The method according to claim 1, wherein the α-olefin polymerization catalyst component is propylene polymerization catalyst component.

10. The method according to claim 9, wherein the propylene polymerization catalyst component is prepared by reacting magnesium chloride-alcohols complex compound carrier with titanium tetrachloride and the internal electron donor compound.

11. The method according to claim 10, wherein the steps for preparing propylene polymerization catalyst component using magnesium chloride-alcohols complex compound carder with titanium tetrachloride and the internal electron donor compound are as follows:
providing a magnesium chloride-alcohols complex compound,
mixing the magnesium chloride-alcohols complex compound with titanium tetrachloride at a ratio of 1 gram: 15-25 mL at the temperature of −20° C. to −10° C., with stirring and heating them to 110° C., and
adding the electron donor compound during the heating process of 30° C. to 110° C., then allowing a reaction to undergo 1-3 hours at 110° C., followed by filtering and then adding the same amount of titanium tetrachloride to react 1-3 hours at the temperature of 110° C. to 120° C., and finally washing and drying the product to obtain the propylene polymerization catalyst component.

12. The method according to claim 9, wherein the propylene polymerization catalyst component is directly prepared by reacting magnesium chloride, alcohols, the internal electron donor compound and titanium tetrachloride.

\* \* \* \* \*